US00PP23707P2

(12) United States Plant Patent
Nielsen

(10) Patent No.: US PP23,707 P2
(45) Date of Patent: Jul. 2, 2013

(54) *DAHLIA* PLANT NAMED 'DAENOGTYVE'

(50) Latin Name: *Dahlia Cav.*
Varietal Denomination: DAENOGTYVE

(75) Inventor: Rune Harboe Nielsen, Grönnegyden (DK)
(73) Assignee: Dalina Genetics APS, Odense N (DK)

( * ) Notice: Subject to any disclaimer, the term of this patent is extended or adjusted under 35 U.S.C. 154(b) by 0 days.
(21) Appl. No.: 13/374,957
(22) Filed: Jan. 25, 2012
(51) Int. Cl.
*A01H 5/00* (2006.01)
(52) U.S. Cl.
USPC ..... Plt./321
(58) Field of Classification Search
USPC ..... Plt./321
See application file for complete search history.

(56) References Cited

PUBLICATIONS

Printout of application information from Community Plant Variety Office (CPVO) website for corresponding CPVO application No. 2011/1745 filed Jul. 8, 2011 (1 page) (http://www.cpvoextranet.cpvo.europa.eu).

Printout of application information for Canadian Plant Breeders' Rights application No. 11-7379 filed Oct. 6, 2011, published in Plant Varieties Journal No. 82, Jan. 2012 (1 page) (www.inspection.gc.ca/plants/plant-breeders-rights/plant-varieties-journal).

*Primary Examiner* — Annette Para
(74) *Attorney, Agent, or Firm* — Foley & Lardner LLP

(57) ABSTRACT

A new distinct cultivar of *Dahlia* plant named 'DAENOGTYVE', characterized by its upright to slightly spreading shape, with stiff and strong lateral stems and thick compound leaves, with up to 12 leaflets. The color of the mature leaves are RHS Yellow-green 147A (upper side) and RHS Grayed-green 191A (Underside). Compound leaves are 8-24 cm in length, and 8-18 cm in width. Only a few single leaves peduncle are present. Composite flower heads are 10-12 cm in diameter, with a large number of ray florets (about 150 to 200). The ray florets are white near base to RHS Red-purple N74A. The amount of white on the ray floret differs from 20%-50% (a few even 80%).

7 Drawing Sheets

Latin name of the genus and species of the claimed plant: *Dahlia Cav.*

Variety denomination: 'DAENOGTYVE'.

BACKGROUND OF THE INVENTION

The present invention relates to a new and distinct cultivar of *Dahlia* plant, botanically known as *Dahlia Cav.*, of the *Compositae* (*Asteraceae*) family, hereinafter referred to by the cultivar name 'DAENOGTYVE'.

The new *Dahlia* cultivar is a product of a planned breeding program conducted by the inventor, Rune Nielsen, in Stige, Denmark. The objective of the breeding program is to develop a new *Dahlia* cultivar with an upright, strong and healthy growth habit, suitable for large scale container production and with good garden performance; fully double flowers creating globular-shaped flower head (composite flower heads with many ray florets) with an attractive inflorescence color.

The new *Dahlia* cultivar originated from a cross, made in a controlled breeding program by the inventor in 2008, in Stige, Denmark. The female or seed parent is a Red-purple *Dahlia* designated 5876G (Breeder's Reference; unpatented). The male or pollen parent is a light Purple-violet *Dahlia* designated 5187C (Breeder's Reference; unpatented).

Asexual reproduction of the new *Dahlia* cultivar by terminal cuttings was first performed in September, 2009 in Stige, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DAENOGTYVE', which in combination distinguish this *Dahlia* as a new and distinct cultivar:

1. Cultivar, with upright to slightly spreading shape;
2. Cultivar with stiff and strong lateral stems and thick compound leaves, with up to 9 leaflets. Color of mature leaves RHS 147A (upper side) RHS 191A (Underside);
3. Compound leaves with 2 to 12 leaflets, 8-24 cm in length, and 8-18 cm in width, with only a few single leaves present near peduncle;
4. Composite flower heads, 10-12 cm in diameter, with a large number of ray florets (about 150 to 200); and
5. Ray floretsare white near base to RHS Red-purple N74A; the amount of white on the ray florets differs from 20%-50% (a few even 80%).

Plants of the new *Dahlia* 'DAENOGTYVE' differ from plants of the parent, in the traits described in Table 1.

(The male and female parents are no longer available for a detailed evaluation. The evaluation is therefore based on historical data)

TABLE 1

Comparison with Parental Varieties

| Trait | New Cultivar 'DAENOGTYVE' | Comparison Cultivar 5876G Female parent | Comparison Cultivar 5187C Male parent |
|---|---|---|---|
| Plant Size | | | |
| Height: | About 35-45 cm. | About 25-35 cm. | About 50-55 cm. |
| Diameter: | About 45-50 cm. | About 30-40 cm. | About 45-50 cm. |
| Overall Plant Shape: | Upright to spreading with basal branching. Inflorescences in composite heads. | Upright to spreading with basal branching. Inflorescences in composite heads. | Upright to spreading with basal branching. Inflorescences in composite heads. |

TABLE 1-continued

| Comparison with Parental Varieties | | | |
|---|---|---|---|
| Trait | New Cultivar 'DAENOGTYVE' | Comparison Cultivar 5876G Female parent | Comparison Cultivar 5187C Male parent |
| Basal branches with flowers | | | |
| Length: | 30-40 cm. | 20-30 cm. | 45-50 cm. |
| Diameter: | 12-16 mm | 10-12 mm. | 10-16 mm. |
| Strength: | Stiff and strong. | Stiff and strong. | Stiff and strong. |
| Color: | Mature: RHS Yellow-green 146B. Immature: RHS Yellow-green 146C. | Yellow-green. | Yellow-green. |
| Leaves | | | |
| Color mature upper side: | RHS Yellow-green 147A. | Dark-green. | Dark-green. |
| Underside: | RHS Grayed-green 191A. | | |
| Peduncle | | | |
| Color mature: | RHS Yellow-green 144A. | Yellow-green | Yellow-green. |
| Color immature: | RHS Yellow-green 144A. | Brown at sun exposed parts. | |
| Color of ray florets Upper side: | White near base to RHS Red-purple N74A. The amount of white on ray floret differs from 20-50% (a few even 80%). | Red-purple. | Light Purple-violet. |

Of the many commercial cultivars known to the present inventor, the most similar in comparison to the new *Dahlia* 'DAENOGTYVE' is the *Dahlia* cultivar 'DAELLEVE' (Patented, U.S. Plant Pat. No. 19,184), in the characteristics described in Table 2:

TABLE 1

| Comparison with Comparison Varieties | | | |
|---|---|---|---|
| Trait | New Cultivar 'DAENOGTYVE' 6653P | New Cultivar 'DATREOGTYVE' 6653E | Comparison Cultivar 'DAELLEVE' |
| Plant Size | | | |
| Height: | About 35-45 cm. | About 40-50 cm. | About 40-45 cm. |
| Diameter: | About 45-50 cm. | About 45-50 cm. | About 40-45 cm. |
| Overall Plant Shape: | Upright to spreading with basal branching. Inflorescences in composite heads. | Upright to spreading with basal branching. Inflorescences in composite heads. | Cylindrical, a little spreading, with basal branching. Inflorescences in composite heads. |
| Basal branches with flowers | | | |
| Length: | 30-40 cm. | 35-45 cm. | 25-40 cm. |
| Diameter: | 12-16 mm | 12-16 mm | 8-12 mm |
| Strength: | Stiff and strong. | Stiff and strong. | Stiff and strong. |
| Color: | Mature: RHS Yellow-green 146B. | Mature: RHS Yellow-green 146B. | RHS Brown 200B. |

TABLE 1-continued

| Comparison with Comparison Varieties | | | |
|---|---|---|---|
| Trait | New Cultivar 'DAENOGTYVE' 6653P | New Cultivar 'DATREOGTYVE' 6653E | Comparison Cultivar 'DAELLEVE' |
| | Immature: RHS Yellow-green 146C. | Immature: RHS Yellow-green 146C. | |
| Leaves | | | |
| Colour mature upper side: | RHS Yellow-green 147A. | RHS Yellow-green 147A. | RHS Green 139A. |
| Underside: | RHS Grayed-green 191A. | RHS Grayed-green 191A. | RHS Grayed-green 191B. |
| Peduncle | | | |
| Colour mature: | RHS Yellow-green 144A. | RHS Yellow-green 146A. | RHS Brown 200B |
| Colour immature: | RHS Yellow-green 144A. | Sun exposed parts will get some brownish as dark as RHS Brown 200C. | RHS 146B |
| Color of ray florets Upper side: | White near base to RHS Red-purple N74A. The amount of white on ray floret differs from 20-50% (a few even 80%). | Third near base: RHS White 155C Two third near apex: RHS Violet 84B. | Base: Purple 67A. Tip: Red-purple 62D. |

BRIEF DESCRIPTION OF THE PHOTOGRAPHS

The accompanying photographs illustrate the overall appearance of the new *Dahlia* 'DAENOGTYVE' showing the colors as true as is reasonably possible with colored reproductions of this type. Colors in the photographs may differ slightly from the color value cited in the detailed botanical description, which accurately describe the color of 'DAENOGTYVE'.

DETAILED BOTANICAL DESCRIPTION

Figure 1:
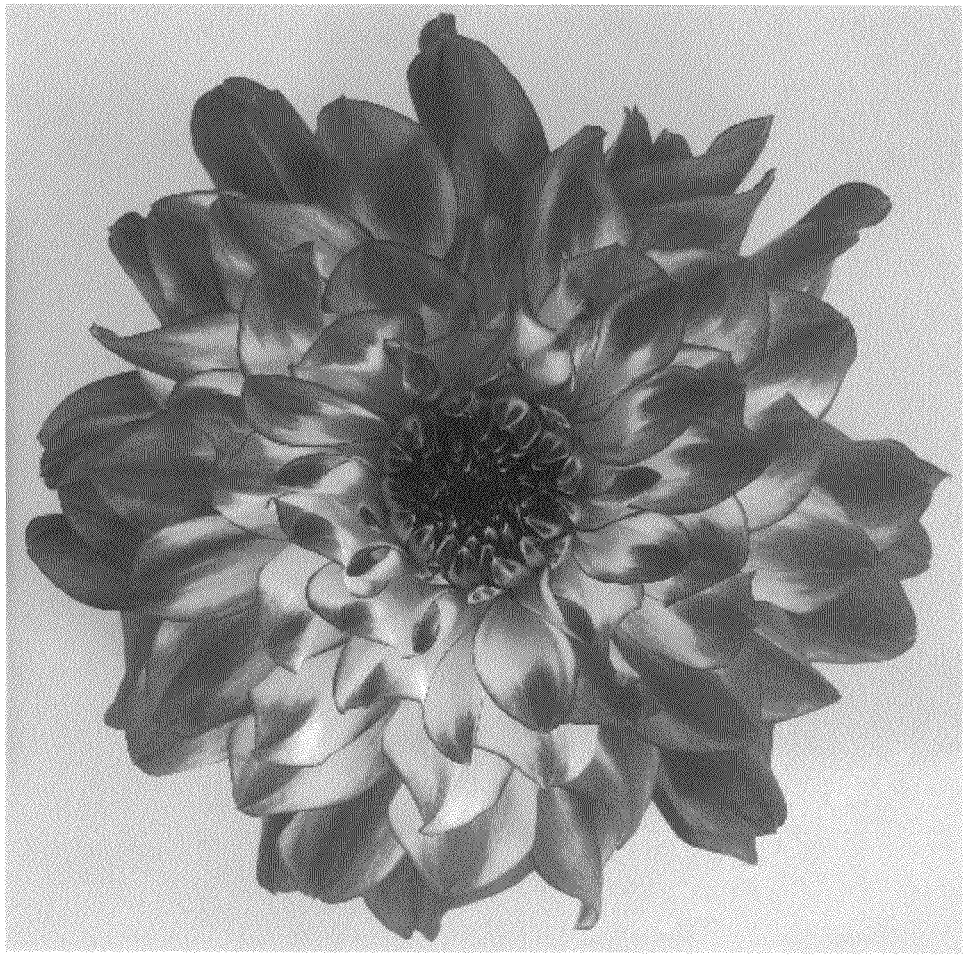
FIG. 1 shows a close-up view of the composite flower head from 'DAENOGTYVE'.
Figure 2:
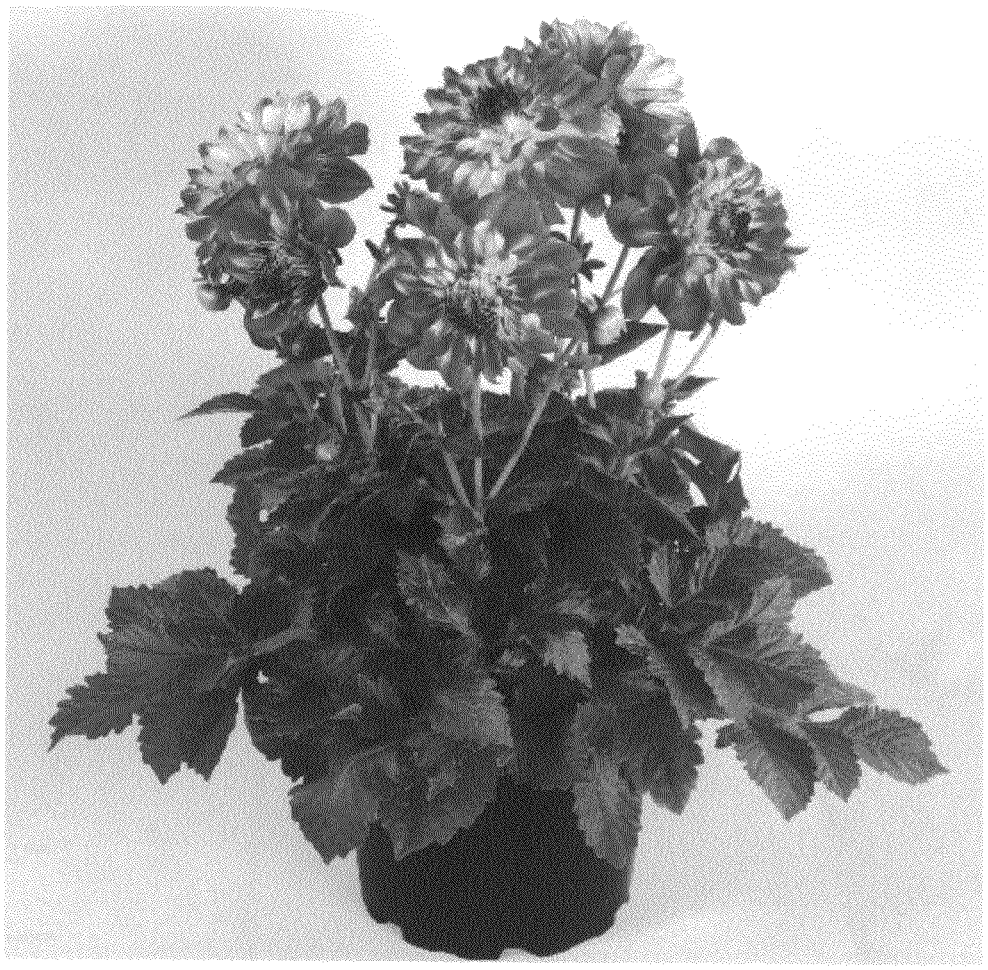
FIG. 2 shows a side view perspective of a typical flowering plant of 'DAENOGTYVE' in a 19 cm pot, at 8 weeks of age after potting the young plant.
Figure 3:
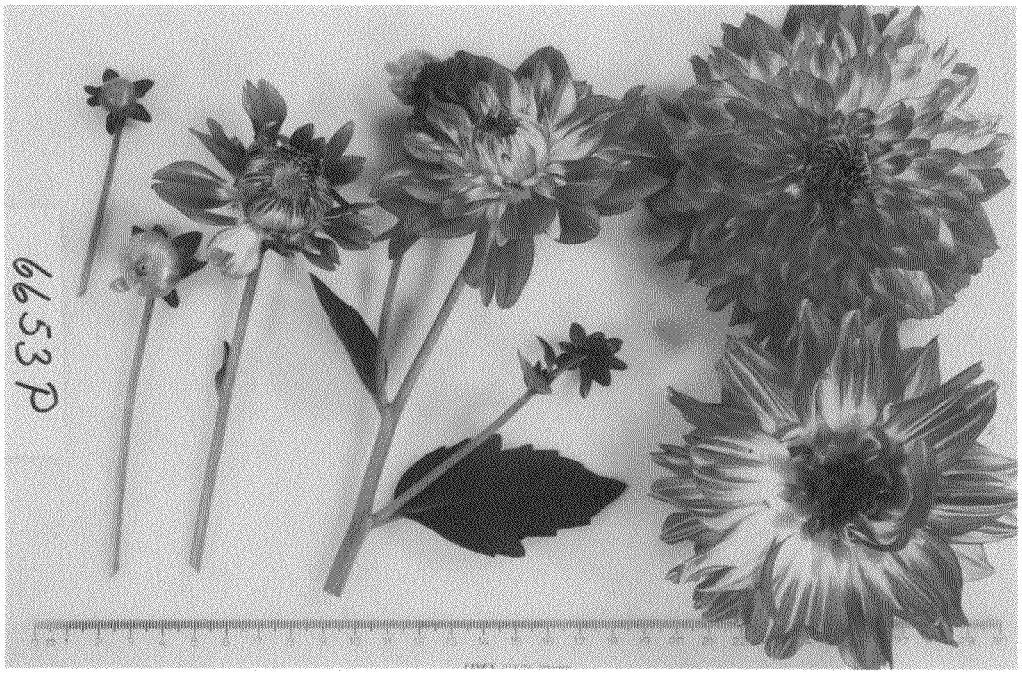
FIG. 3 shows a close-up view of different development stages of the composite flower head of 'DAENOGTYVE'.
Figure 4:
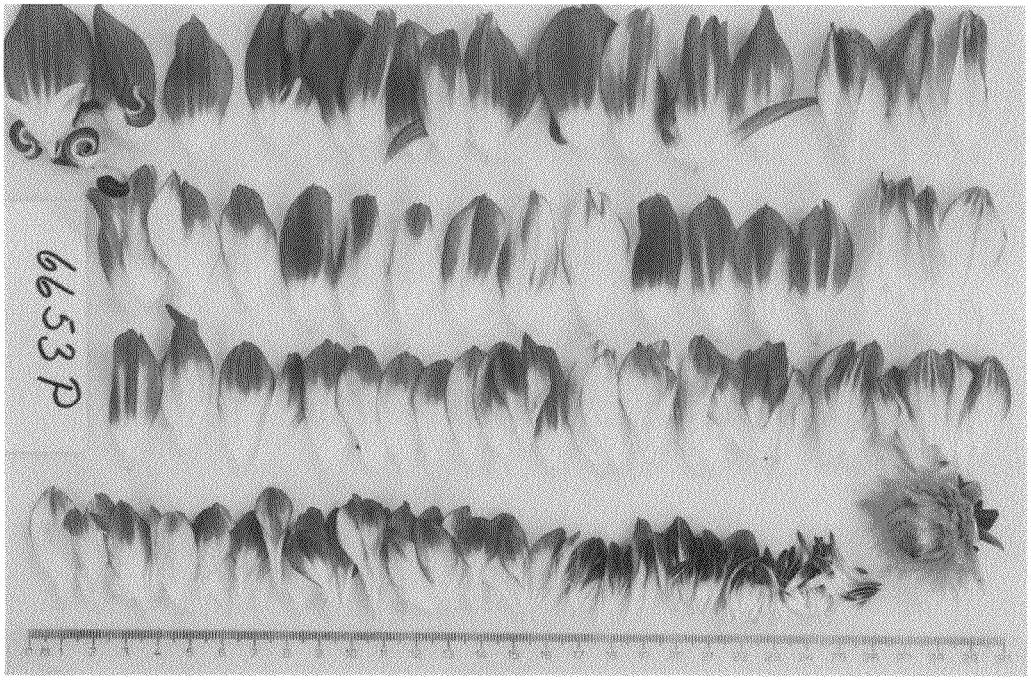
FIG. 4 shows a close-up view of the 150-200 ray florets from one composite flower head of 'DAENOGTYVE'
Figure 5:
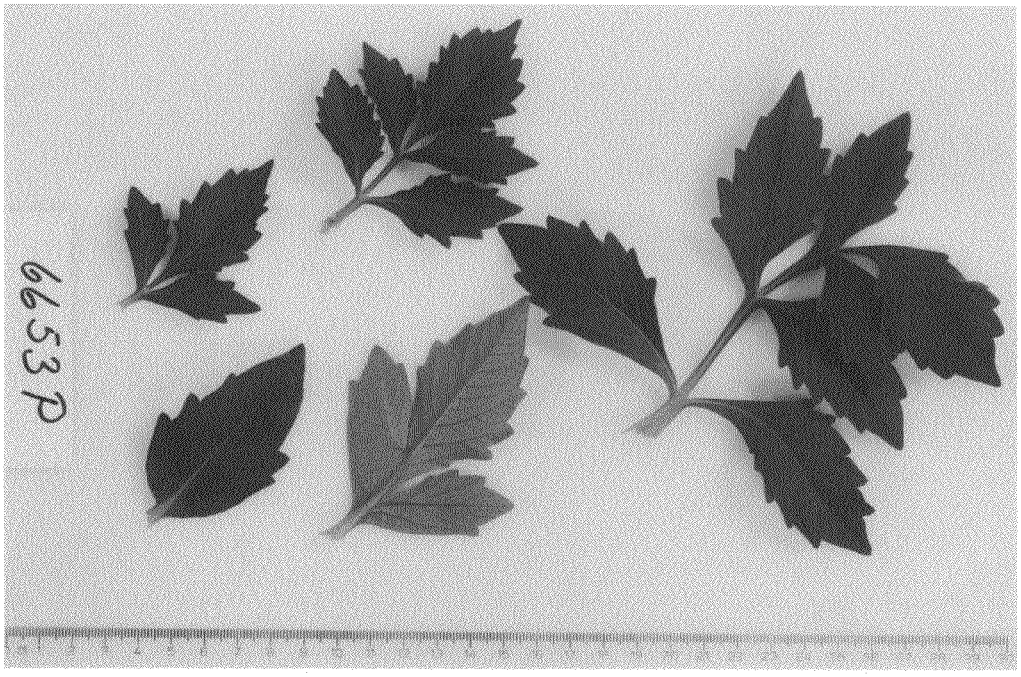
FIGS. 5 and 6 show a close-up view of the different compound and single leaf sizes of 'DAENOGTYVE'.
Figure 6:
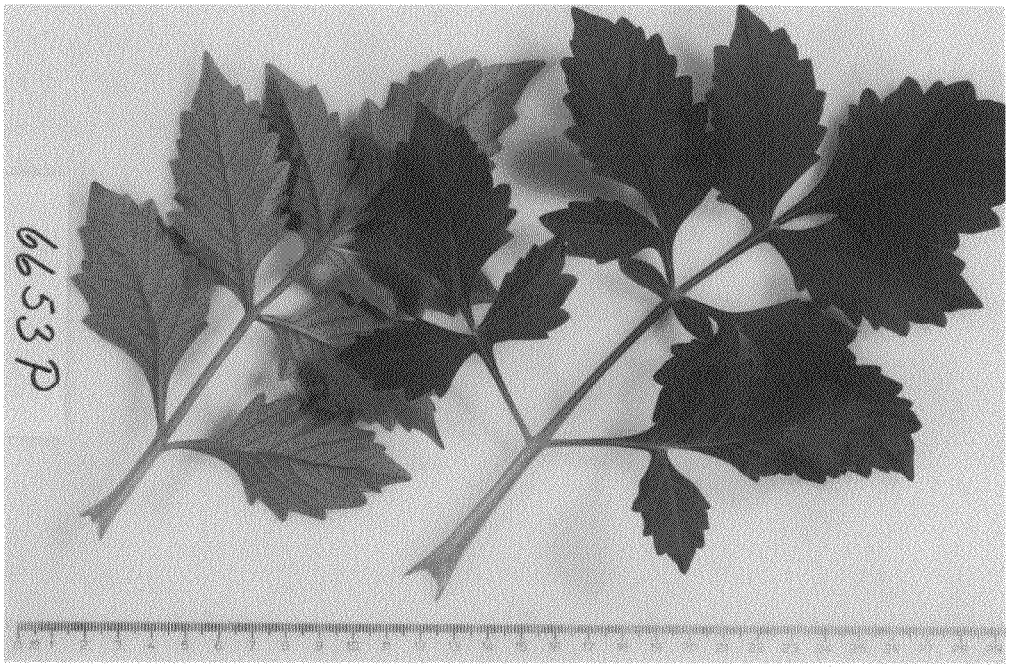
Figure 7:
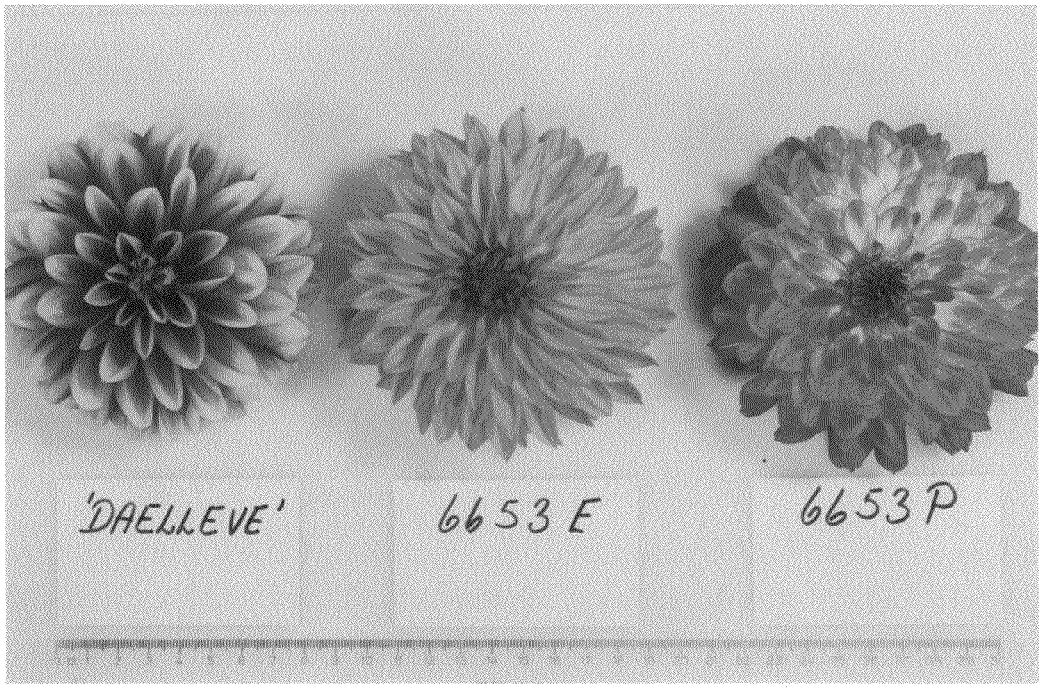
FIG. 7 shows a comparison between 'DAELLEVE', 'DATREOGTYVE' (Breeders reference: 6653E) and 'DAENOGTYVE', (Breeders reference: 6653P).

The new *Dahlia* 'DAENOGTYVE' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Dahlia* 'DAENOGTYVE' as grown in a protected environment in a glass, greenhouse in Fyn, Odense, Denmark, under conditions which closely approximate those generally used in commercial practice. During propagation, conducted in a glasshouse, vegetative cuttings were planted 6 Jul. 2011 in small propagation pots with peat as substrate, and then placed in a plastic tunnel averaging about 21° C. and received photoperiodic treatments of 18 hours. Supplementary light was given when natural light fell below 3000-4000 Lux. Rooting occurred about 12 days after planting. In third week after planting the cutting (27 Jul. 2011), young plants were potted in an 19 cm pot in a glass covered greenhouse, maintained at 18° C. to 26° C. during the day, and at 17° C. to 19° C. during the night. Plants were grown under natural daylight conditions. Irrigation was done with water. The EC measured in the soil was maintained between 2.0 to 3.0. One week after potting, the first growth regulation was given: a spray with 85% daminozide, 0.2%, 40-100 m1/m2. During the production time, 9 additional sprayings were given with 85% daminozide, 0.2%, 40-100 m1/m2.

Color references are made to The Royal Horticultural Society Colour Chart (R.H.S.), 2001 edition, except where general colors of ordinary significance are used. Color values were taken under September daylight conditions at approximately 12:00 PM and 2:00 PM in Fyn, Odense, Denmark. The age of the 'DAENOGTYVE' plants described is 10-11 weeks (including propagation time).

Classification:

*Botanical.*—*Dahlia Cav.*

Parentage:

*Female or seed parent.*—*Dahlia* designated 5876P.

*Male or pollen parent.*—*Dahlia* designated 5187C.

Propagation:

*Type.*—Vegetative terminate cuttings.

*Time and temperature to initiate roots.*—About 9 to 12 days at 21° C. in tunnels or flat covered in a greenhouse.

*Time and temperature to produce a rooted young plant.*—About 21 days at 21° C. during rooting phase, followed by 18° C.

*Rooting habit.*—Fine, fibrous; Color of root: RHS Yellow-white 158C.

*Tuber development.*—Plants might develop tubers in late fall when planted outside.

Plant description:

*General appearance and form.*—Upright to slightly spreading shape. Inflorescences in composite heads.

*Growth rate.*—Growing about 3 to 5 cm per week during production period.

*Plant height* (*from soil level to top of plant plane*).—About 35-45 cm.

*Plant width* (*spread*).—About 45-50 cm.

*Crop time to produce a mature flowering plant.*—It requires 3 to 4 weeks to produce a young plant in a 35 mm propagation plug. After potting 7 to 11 weeks are required to produce finished flowering plants in 19 cm pots.

Stem:

*Shape.*—Round.

*Length* (*pinched above* 3 *pair of leaves*).—About 3-5 cm.

*Diameter.*—About 12-15 mm.

*Strength.*—Stiff and strong.

*Aspect.*—Upright.

*Texture.*—Fluted woody surface.

*Color.*—RHS Yellow-green 146C turning to RHS Gray-brown 199C.

Branches:

*Branching habit.*—Basal branching with lateral branches.

*Number of basal branches per plant.*—About 3-5 (when pinched above 3 pair of leaves).

*Length* (*including flowers*).—About 30-40 cm.

*Diameter.*—About 12-16 mm.

*Strength.*—Stiff and strong.

*Aspect.*—Upright to slightly spreading.

*Texture.*—Smooth and glabrous.

*Color.*—Mature: RHS Yellow-green 146B. Immature: RHS Yellow-green 146C.

*Internodes length.*—About 15-40 mm.

*Internodes color.*—RHS Yellow-green 146B.

Foliage description:

*Type.*—Compound leaves divided into 2-12 leaves. Only very few single leaves present.

*Number of leaves per branch.*—About 8-12 per branch.

*Color of leaves* (*leaves and leaflets*).—Color of upper side (mature) RHS 147A. Color of underside (mature) RHS 191A. Color of upper side (immature) RHS 137A. Color of underside (immature) RHS 137C.

*Venation* (*leaves and leaflets*).—Pattern: Pinnate. Color of upper side: RHS 146A. Color of underside: RHS 146B.

Compound leaves:

*Number of leaflets per compound leaf.*—3-9.

*Length of compound leaf.*—8-24 cm.

*Width of compound leaf.*—8-18 cm.

*Petiole of compound leaves.*—Shape: Semi circular, with deep furrow on adaxial side. Length: 4-7 cm. Diameter: 3-10 mm. Texture: Smooth and glabrous. Color: RHS Yellow-green 146B to RHS Yellow-green 147A.

*Leaflets of compound leaf.*—Terminal leaflet quantity: 1. Terminal leaflet length: 6-12 cm. Terminal leaflet width: 5-7 cm. Terminal leaflet shape: Ovate. Terminal leaflet shape at apex: Acuminate. Terminal leaflet shape at base: Cordate to rounded (not always symmetric). Terminal leaflet margin: Dentate. Terminal leaflet texture (both sides): Rugose. Rachis length: 1-8 cm. Rachis Diameter: 2-4 mm. Rachis color: Upper side: RHS Yellow-green 147A. Under side: RHS Yellow-green 146B. Lateral leaflet quantity: 2-6. Lateral leaflet length: 3-10 cm. Lateral leaflet width: 3-6 cm. Lateral leaflet overall shape: Ovate. Lateral leaflet shape at apex: Acuminate (not always symmetric.) Lateral leaflet shape at base: Rounded (not always symmetric). Lateral leaflet margin: Dentate. Lateral leaflet texture (both sides): Rugose Simple leaves: Only small leaves near the composite flower heads.

*Simple leaves overall shape.*—Ovate.

*Simple leaves shape at apex.*—Acute.

*Simple leaves shape at base.*—Rounded.

*Simple leaves length.*—6-8 cm.

*Simple leaves width.*—4-6 cm.

*Simple leaves margin.*—Dentate.

*Simple leaves texture.*—Rugose.

*Petiole shape.*—Semi circular, with deep furrow on adaxial side.

*Petiole length.*—0-1 cm.

*Petiole diameter.*—3-5 mm.

*Petiole texture.*—Smooth and glabrous.

*Petiole color*.—RHS Yellow-green 146B to RHS Yellow-green 147A.

Inflorescence description:

*Natural flowering season*.—Grown outside as a bedding plant, flowering occurs continuously during growing season from spring to autumn/(In Denmark, from June to beginning of October). Plants can be brought to flower anytime when grown under the recommended greenhouse conditions.

*Time to flower*.—50 to 80 days from potting a young plant until flowering.

*Inflorescence longevity on the plant*.—Inflorescence will maintain good color and substance for about 6-10 days; however, the longevity of individual inflorescence is highly dependent on temperature and light conditions. Inflorescence persistent.

*Type*.—Composite flower heads.

*Arrangement and shape*.—Persistent, single, composite inflorescences from leaf axils. Disc and ray florets arranged acropetally in a composite flower head. Upright, slightly spreading. Terminal young flower head/buds initially 80-100°. Buds from axillary shoots 80-100°. When flower opens 70-90°.

*Quantity of inflorescences heads*.—Freely flowering; about 18 buds and open inflorescences per plant.

*Fragrance*.—None.

*Bud* (*inflorescences head*).—Rate of opening (from showing color to fully open): 4 to 10 days. The rate of opening is highly dependent on temperature and light conditions. Length: About 10-14 mm. Diameter: About 18-24 mm. Shape: Flat globular. Texture: Glabrous, shining. Color: RHS Yellow-green 144A to Yellow-green N144A before opening.

*Peduncle*.—From both terminate and axillary shoots. Length: About 12-16 cm. Diameter: About 4-6 mm. Angle: About 0-20° from vertical. Strength: Stiff and strong. Texture: Glabrous. Color (mature/immature): RHS Yellow-green 144A.

*Inflorescence head*.—Depth (height): 4-7 cm. Diameter: 10-12 cm.

*Ray florets*.—Arrangement: Imbricate, in about 12 to 14 whorls of ray florets, each with 12 to 18 florets to equal a total of about 150-200 ray florets per flower head, depending on light and temperature conditions. Quantity per Inflorescence head: 150-200. Length: 45-52 mm. Widths: 26-32 mm. Overall shape: Obovate. Apex shape: Obtuse. A few ray florets have 1-3 irregular 2-15 mm deep clefts near apex. Base shape: Acuminate, slightly fused. Margin: Entire, apart from a few ray florets that have 1-3 irregular 2-15 mm deep clefts near apex. Texture: Upper side: Glabrous. Under side: Pubescent (small and few). Colour when opening fused ray floret starting to show color: RHS Purple-violet N81A. Colour when fully opened Color upper side: White near base to RHS Red-purple N74A. The amount of white on ray floret differs from 20-50% (a few even 80%). Color underside: RHS Red-purple N74A, with white stripes along veins and scattered spots.

*Disc florets*.—Arrangement: 50-65 yellow-orange disc florets arranged in center of inflorescence head. Apperance: Quantity per Inflorescence head: 50-65. Length: 7-10 mm. Diameter: 2 mm. Overall shape: Tubular. Apex shape: Star with 5 triangular tips. Base shape: Fused to tube. Color RHS Yellow-orange 21A.

*Phyllary*.—Arrangement: One subtending each floret. Quantity: 200-265. Length: 10-22 mm. Width: 5-8 mm. Overall shape: Rounded. Shape at apex: Acute with rounded tip. Shape at base: Fused. Margin: Entire. Color: Mature: RHS Yellow-green 151C. RHS Yellow-green 146A on underside near base of the phyllaries in the outer whorl, Color: Immature: RHS Yellow-green 151C.

*Brachts*.—Arrangement and appearance: Reflexed, involucral bracts. Quantity: 7-8. Length: 14-20 mm. Width: 6-8. Overall shape: Subulate. Apex shape: Acute. Base shape: Sessile. Margin: Entire. Texture: Glabrous. Colour mature Upper side: RHS 137B. Underside: RHS 137C. Colour immature Upper side: RHS 137B. Underside: RHS 137C.

Reproductive organs:

*Androecium*.—Location: Disc florets only. Stamen number: 5, fused into synandrous tube around style. Stamen length: About 5-7 mm. Anther shape: Tubular. Anther length: About 2-4 mm. Pollen amount: Some. Pollen color: RHS N25C.

*Gynoecium*.—Poorly developed and not present on all flowers. The outer whorls of ray florets and the disc florets have the most developed Gynoeciums. Location: Ray and disc florets. Quantity: Up to 1. Pistil length: 7-8 mm. Stigma shape: Bifurcate. Stigma length: About 2 mm. Stigma color: Not visible due to the cover of pollen brushed of the anthers. It then appears RHS N25C. Style length: About 3 mm. Style color: RHS 151C. Ovary color: RHS 151C.

Seed/fruit: Seed and fruit production has not been observed.

Disease/pest resistance: Resistance to pathogens and pests common to *Dahlia* has not been observed.

Disease/pest susceptibility: Susceptibility to pathogens and pests common to *Dahlia* has not been observed.

Temperature tolerance: Plants of the new *Dahlia* have exhibited good tolerance rain, wind and drought; however, flowering may cease during hot periods (temperatures above 25° C.). Low temperature tolerance to 1° C.

Growth regulators: Daminozide (85% water soluble dryconcentrate formulation).

What is claimed is:

1. A new and distinct cultivar of *Dahlia* plant named 'DAENOGTYVE', as illustrated and described herein.

* * * * *